United States Patent
Skoglund et al.

(10) Patent No.: US 10,073,174 B2
(45) Date of Patent: Sep. 11, 2018

(54) SENSING APPARATUS USING MULTIPLE ULTRASOUND PULSE SHAPES

(71) Applicant: DolphiTech AS, Raufoss (NO)

(72) Inventors: Eskil Skoglund, Gjøvik (NO); Arnt-Børre Salberg, Hamar (NO); Tore Baarstad, Lillehammer (NO)

(73) Assignee: DolphiTech AS, Raufoss (NO)

( * ) Notice: Subject to any disclaimer, the term of this patent is extended or adjusted under 35 U.S.C. 154(b) by 892 days.

(21) Appl. No.: 14/489,835

(22) Filed: Sep. 18, 2014

(65) Prior Publication Data

US 2015/0078129 A1 Mar. 19, 2015

(30) Foreign Application Priority Data

Sep. 19, 2013 (GB) .................... 1316656.6

(51) Int. Cl.
 *G01S 15/00* (2006.01)
 *G01S 15/02* (2006.01)
 (Continued)

(52) U.S. Cl.
 CPC ............ *G01S 15/02* (2013.01); *G01N 29/043* (2013.01); *G01N 29/343* (2013.01); *G01N 29/4436* (2013.01); *G01S 7/5202* (2013.01); *G01S 7/5205* (2013.01); *G01S 7/52026* (2013.01); *G01S 7/52046* (2013.01);
 (Continued)

(58) Field of Classification Search
 USPC ........................................................ 367/87
 See application file for complete search history.

(56) References Cited

U.S. PATENT DOCUMENTS 2,804,614 A * 8/1957 Alvarez ................ G01S 7/2813
 342/147
3,723,952 A * 3/1973 Walsh ................... G01S 7/2921
 342/378
(Continued)

FOREIGN PATENT DOCUMENTS

CN 102599929 A * 7/2012 ........... A61B 8/5269
CN 102680583 9/2012
(Continued)

OTHER PUBLICATIONS

Jorg, K-W., and Markus Berg. "First results in eliminating crosstalk and noise by applying pseudo-random sequences to mobile robot sonar sensing." Advanced Mobile Robot, 1996., Proceedings of the First Euromicro Workshop on. IEEE, 1996.*
(Continued)

*Primary Examiner* — Isam A Alsomiri
*Assistant Examiner* — Jonathan D Armstrong
(74) *Attorney, Agent, or Firm* — Fish & Richardson P.C.

(57) ABSTRACT

A sensing apparatus comprising an ultrasound transceiver for transmitting ultrasound signals into a sample and receiving a resultant ultrasound reflection signal from the sample, a detector for processing signals received by the transceiver by comparing the received signal against a reference signal to generate a response signal, the response signal comprising values as a function of time that represent the strength of the match between the received signal and the reference signal at the respective time; and a driver capable of generating a plurality of pre-defined pulse templates.

22 Claims, 8 Drawing Sheets

Typical signal pulse

Match filter corresponding to the pulse in Figure 1

(51) Int. Cl.
  *G01N 29/34* (2006.01)
  *G01S 7/52* (2006.01)
  *G01N 29/04* (2006.01)
  *G01N 29/44* (2006.01)

(52) U.S. Cl.
  CPC .... *G01N 2291/044* (2013.01); *G01S 7/52085* (2013.01); *Y10T 29/49004* (2015.01)

(56) References Cited

U.S. PATENT DOCUMENTS

| | | | |
|---|---|---|---|
| 3,778,756 A | | 12/1973 | Houston |
| 3,895,525 A | | 7/1975 | Eichelberger et al. |
| 4,159,462 A | * | 6/1979 | Rocha ............... G01S 7/52026 367/105 |
| 4,325,257 A | * | 4/1982 | Kino ............... G01N 29/262 367/123 |
| 4,441,369 A | | 4/1984 | Lessard et al. |
| 5,235,985 A | * | 8/1993 | McMorrow ............ A61B 5/204 128/916 |
| 5,383,366 A | | 1/1995 | Wallingford et al. |
| 5,396,890 A | | 3/1995 | Weng |
| 5,497,661 A | | 3/1996 | Stripf |
| 5,773,811 A | | 6/1998 | Schramm, Jr. et al. |
| 6,099,472 A | * | 8/2000 | Fukukita ............ G01S 7/52038 600/443 |
| 6,748,259 B1 | | 6/2004 | Benaron |
| 7,675,045 B1 | | 3/2010 | Werner |
| 8,453,928 B2 | | 6/2013 | Melandsø et al. |
| 9,470,662 B2 | | 10/2016 | Baarstad et al. |
| 2002/0062083 A1 | | 5/2002 | Ohara et al. |
| 2002/0130807 A1 | * | 9/2002 | Hall ............... G01S 7/282 342/28 |
| 2003/0145655 A1 | | 8/2003 | Lorraine et al. |
| 2005/0279171 A1 | | 12/2005 | Kollgaard |
| 2006/0126434 A1 | * | 6/2006 | Intrator ............... G01S 7/52004 367/135 |
| 2006/0219013 A1 | | 10/2006 | Baba et al. |
| 2007/0053795 A1 | | 3/2007 | Laugharn |
| 2007/0084290 A1 | | 4/2007 | Fetzer et al. |
| 2008/0000299 A1 | | 1/2008 | Georgeson |
| 2008/0009739 A1 | * | 1/2008 | Chiang ............... A61B 8/4483 600/459 |
| 2008/0208061 A1 | | 8/2008 | Halmann |
| 2009/0082673 A1 | | 3/2009 | Lu et al. |
| 2010/0274139 A1 | | 10/2010 | Fukukita et al. |
| 2011/0040187 A1 | | 2/2011 | Matsumura |
| 2012/0192651 A1 | | 8/2012 | Lee et al. |
| 2013/0030727 A1 | | 1/2013 | Zalameda et al. |
| 2015/0049579 A1 | | 2/2015 | Skoglund et al. |
| 2015/0049580 A1 | | 2/2015 | Skoglund et al. |
| 2015/0053013 A1 | | 2/2015 | Baarstad et al. |

FOREIGN PATENT DOCUMENTS

| | | | |
|---|---|---|---|
| CN | 104656074 A | * | 5/2015 |
| DE | 20213105252 | | 4/2014 |
| EP | 1621135 | | 11/2006 |
| EP | 2249152 | | 11/2010 |
| GB | 2109555 | | 6/1983 |
| GB | 2286678 | | 8/1995 |
| GB | 2432671 | | 5/2007 |
| JP | 60-102553 | | 6/1985 |
| JP | 60-102554 | | 6/1985 |
| JP | 08-075714 | | 3/1996 |
| JP | 2006284241 A | * | 10/2006 |
| JP | 2010060520 A | | 3/2010 |
| WO | WO2008/137030 | | 11/2008 |
| WO | WO2011/089537 | | 7/2011 |
| WO | WO2013/161834 | | 10/2013 |

OTHER PUBLICATIONS

S.N. Narouze (ed.), Atlas of Ultrasound-Guided Procedures in Interventional Pain Management, 13 DOI 10.1007/978-01-4419-1681-5_2,Chapter 2 Basics of Ultrasound Imaging Vincent Chan and Anahi Perlas, © Springer Science+ Business Media, LLC 2011. (Year: 2011).*

Gustafsson, M. G., et al., "Split Spectrum Algorithms Rely on Instantaneous Phase Information—A Geometrical Approach," IEEE Transactions on Ultrasonics, Ferroelectrics, and Frequency Control, vol. 40, No. 6, Nov. 1993, pp. 659-665.

Niblack, Wayne, "Digital Image Processing," 1986 Prentice-Hall International, 217 pages.

Rubbers, Philippe, et al., "An Overview of Split Spectrum Processing," NDT.net Aug. 2003, vol. 8, No. 8, http://www.ndt.net/article/v08n08/rubbers.htm, 10 pages.

Stoica, Petre, et al., "Transmit Codes and Receive Filters for Radar," IEEE Signal Processing Magazine, Nov. 2008, pp. 94-109.

Tian, Qi, et al., "Multiple Target Detection Using Split Spectrum Processing and Group Delay Moving Entropy," IEEE Transactions on Ultrasonics, Ferroelectrics, and Frequency Control, vol. 42, No. 6, Nov. 1995, pp. 1076-1086.

Tomasi, C., et al., "Bilateral Filtering for Gray and Color Images," Proceedings of the 1998 IEEE International Conference on Computer Vision, Bombay, India, 8 pages.

Cincotti et al.: "Efficient transmit beamforming in pulse-echo ultrasonic imaging", IEEE Transactions on Ultrasonics, Ferroelectrics and Frequency Control, IEEE, US, vol. 46, No. 6, Nov. 1, 1999, pp. 1450-1458, XP011438016.

Endrerud, Jan Olav; Skoglund, Eskil: "DolphiCam User Manual", Jun. 27, 2013, XP055179749, Raufoss, Noway, http://www.dolphitech.com/wp-content/uploads/2014/12/DolphiCam-User-Manual-1.1-27.06.2013.pdf.

European Extended Search Report issued in EP application No. 14185307.7 dated Apr. 20, 2015, 7 pages.

Persson et al.: "Electric excitation of ultrasound transducers for short pulse generation", Ultrasound in Medicine and Bioligy, New York, NY, US, vol. 7, No. 3, Jan. 1, 1981, pp. 285-289, 291, XP026374039.

[Online] Introduction Videos 1-9, DolphiTech, to be accessed online at <http://www.dolphitech.com/support/14-instruction-videos/22-videos> Aug. 7, 2013.

UK Intellectual Property Office, Search Report, Application No. GB1413618.8, dated Jan. 27, 2015, 4 pages.

UK Intellectual Property Office, Search Report, Application No. GB1413616.2, dated Jan. 28, 2015, 2 pages.

UK Intellectual Property Office, Search Report, Application No. GB1315090.9, dated Jan. 30, 2015, 2 pages.

Data Presentation. (Jun. 25, 2003). Retrieved Jan. 19, 2016, from http://www.nde-ed.org/EducationResources/CommunityCollege/Ultrasonics/EquipmentTrans/DataPres.htm.

Olympus NDT. EPOCH 1000 Series User's Manual. 910-269-EN—Revision B Jun. 2011.

Ultrasound and Ultrasonic Testing. (May 19, 2003). Retrieved Jan. 19, 2016, from http://www.nde-ed.org/EducationResources/HighSchool/Sound/ubraso1.ncl.htm (also believed to be found at http://www.nde-ed.org/EducationResources/HighSchool/Sound/ultrasound.htm).

Hartfield, Cheryl D., and Thomas M. Moore. "Acoustic Microscopy of Semiconductor Packages." Microelectronics Failure Analysis Desk Reference 5 (2004): 268-288.

Regalado, Waldo J. Perez, Andriy M. Chertov, and Roman Gr Maev. "Time of Flight Measurements in Real-Time Ultrasound Signatures of Aluminum Spot Welds: An Image Processing Approach." (2011).

Whitman, John, et al. "Autonomous surgical robotics using 3-D ultrasound guidance: Feasibility study." Ultrasonic imaging 29.4 (2007): 213-219.

[Online] 1 Introduction to DolphiCam, Published on Aug. 7, 2013 by DolphiTech, to be accessed online at <https://www.youtube.com/watch?v=uPZnT78L_PE> Feb. 16, 2016.

[Online] 2 Unboxing, Published on Aug. 7, 2013 by DolphiTech, to be accessed online at <https://www.youtube.com/watch?v=wcvStX941B0> Feb. 16, 2016.

(56) References Cited

OTHER PUBLICATIONS

[Online] 3 The Camera, Published on Aug. 7, 2013, by DolphiTech, to be accessed online at <https://www.youtube.com/watch?v=-G9aJkBdegM> Feb. 16, 2016.
[Online] 4 Getting Started, Published on Aug. 7, 2013 by DolphiTech, to be accessed online at <https://www.youtube.com/watch?v=x_hhrKvGPgk> Feb. 16, 2016.
[Online] 5 Calibrating and Scanning, Published on Aug. 7, 2013 by DolphiTech, to be accessed online at <https://www.youtube.com/watch?v=jNNrN5C-Gz4> Feb. 16, 2016.
[Online] 6 Scanning Boreholes, Published on Aug. 7, 2013 by DolphiTech, to be accessed online at < https://www.youtube.com/watch?v=FUd0SGe9UDg> Feb. 16, 2016.
[Online] 7 Scanning Impact Damages, Published on Aug. 7, 2013 by DolphiTech, to be accessed online at < https://www.youtube.com/watch?v=iI2bDgwL4Yg> Feb. 16, 2016.
[Online] 8 3D Visualization, Published on Aug. 7, 2013 by DolphiTech, to be accessed online at < https://www.youtube.com/watch?v=TGcKxyAq_p0> Feb. 16, 2016.
[Online] 9 Caring for the Camera, Published on Aug. 7, 2013 by DolphiTech, to be accessed online at < https://www.youtube.com/watch?v=LdgmJX9SS0E> Feb. 16, 2016.
Ellingson, William A., J. Scott Steckenrider, and Thomas J. Meitzler. "Defect detection in ceramic armor using phased array ultrasound." Advances in Science and Technology. vol. 65, Trans Tech Publication, 2010.
E.A. Ginzel & R.K. Ginzel. Ultrasonic Properties of a New Low Attenuation Dry Complant Elastomer. NDTnet—Feb. 1996, vol. 1 No. 2, E.A. Ginzel, Materials Research Institute.
Zejak, Boris U., Igor S. Simic, and Aleksa J. Zejak. "Matched and mismatched pulse compression in medical ultrasound imaging." EUROCON'2011, Trends in Communications, International Conference on., vol. 2. IEEE, 2011.
EP Examination Report for corresponding Appl No. 14185307.7, dated Mar. 8, 2018.
Zhenggan Zhou et al: "Application of Pulse Compression Technique in Air-Coupled Ultrasonic Non-Destructive Testing on Composite Material", Proceedings of the 10th European Conference on Nondestructive Testing, Jun. 7, 2010 (Jun. 7, 2010), pp. 1-6, XP055454765, Abingdon.

\* cited by examiner

Typical signal pulse

Match filter corresponding to the pulse in Figure 1

Absolute value of the match filtered ultrasound signal. The upper arrow indicates the amplitude of the main lobe, the middle arrow indicates the amplitude of the largest side lobe and the lower arrow indicates "all" the side lobes that are considered for some of the selection criteria

SENSING APPARATUS USING MULTIPLE ULTRASOUND PULSE SHAPES

CROSS-REFERENCE TO RELATED APPLICATIONS

This application claims priority to UK Patent Application No. 1316656.6 entitled Sensing Apparatus Using Multiple Ultrasound Pulse Shapes, which was filed on Sep. 19, 2013. The disclosure of the forgoing application is incorporated herein by reference in its entirety.

BACKGROUND

This invention relates to a sensing apparatus that outputs ultrasound signals at a sample, receives reflections of those ultrasound signals from the sample and processes the received signals to detect the reflections.

Ultrasound is an oscillating sound pressure wave that can be used to detect objects and measure distances. A transmitted sound wave is reflected and refracted as it encounters materials with different acoustic impedance properties. If these reflections and refractions are detected and analysed, the resulting data can be used to generate images of the environment through which the sound wave traveled.

Ultrasound can be used to identify particular structural features in an object. For example, ultrasound may be used for non-destructive testing by detecting the size and position of flaws in a sample. There are a wide range of applications that can benefit from non-destructive testing, covering different materials, sample depths and types of structural feature, such as different layers in a laminate structure, impact damage, boreholes etc. Therefore, there is a need for a sensing apparatus that is capable of performing well in a wide-range of different applications.

SUMMARY

According to one embodiment, there is provided a sensing apparatus comprising an ultrasound transceiver for transmitting ultrasound signals into a sample and receiving a resultant ultrasound reflection signal from the sample, a detector for processing signals received by the transceiver by comparing the received signal against a reference signal to generate a response signal, the response signal comprising values as a function of time that represent the strength of the match between the received signal and the reference signal at the respective time, and a driver capable of generating a plurality of pre-defined pulse templates, the driver being operable to apply a selected one of the pre-defined pulse templates to the transceiver for driving it to transmit ultrasound signals, the pre-defined pulse templates being such as to include at least two of the following: i) a pulse template that consists of a single pulse and that, when the transceiver is being driven into air, generates a response signal having a higher prominence of a primary peak than the response signals generated by any of the other pre-defined pulse templates that consist of a single pulse; ii) a pulse template that consists of two or more pulses and that, when the transceiver is being driven into air, generates a response signal having a higher prominence of a primary peak than the response signals generated by any of the other pre-defined pulse templates; iii) a pulse template that, when the transceiver is being driven into a solid, generates a response signal having a higher prominence of a primary peak than the response signals generated by any of the other pre-defined pulse templates; and iv) a pulse template that generates a response signal having a higher proportion of its energy in a primary peak than the response signals generated by any of the other pre-defined pulse templates.

Pulse template (i) may generate a response signal in which the ratio of the amplitude of its primary peak to the amplitude of its largest side lobe is higher than in the response signals generated by any of the other pre-defined pulse templates that consist of a single pulse.

Pulse template (i) may generate a response signal in which the difference between the amplitude of its primary peak and the amplitude of its largest side lobe is larger than in the response signals generated by any of the other pre-defined pulse templates that consist of a single pulse.

Pulse template (ii) may generate a response signal in which the ratio of the amplitude of its primary peak to the amplitude of its largest side lobe is higher than in the response signals generated by any of the other pre-defined pulse templates.

Pulse template (ii) may generate a response signal in which the difference between the amplitude of its primary peak and the amplitude of its largest side lobe is larger than in the response signals generated by any of the other pre-defined pulse templates.

Pulse template (iii) may generate a response signal in which the ratio of the amplitude of its primary peak to the amplitude of its largest side lobe is higher than in the response signals generated by any of the other pre-defined pulse templates.

Pulse template (iv) may generate a response signal in which the ratio of the amplitude of its primary peak to the mean absolute energy comprised in its side lobes is higher in than the response signals generated by any of the other pre-defined pulse templates.

The pre-defined pulse templates may include: (v) a pulse template that generates a response signal having an FFT that has an occupied frequency bin with an amplitude that is above a certain value but which is lower than the amplitude of any occupied frequency bin above the certain value in the FFTs of the response signals generated by any of the other pre-defined pulse templates.

Either or both of pulses (iii) and (iv) may consist of a single pulse.

The sensing apparatus may comprise a user input device configured to receive a user input for selecting one of the pre-defined pulse templates to be applied to the transceiver.

The detector may be configured to compare the received signal against a reference signal that is selected in dependence on the selected pulse template.

The detector may be configured to compare the received signal against a match filter.

The pre-defined pulse templates may include a pulse template consisting of two or more pulses of the same length.

The pre-defined pulse templates may include a pulse template consisting of two or more pulses in which the length of one of those pulses is different from the length of at least another of those pulses.

The pre-defined pulse templates include a pulse template consisting of a single step.

According to a second embodiment, there is provided a method of manufacturing a sensing apparatus comprising designing the apparatus, including: testing a plurality of pre-defined pulse templates by driving each pre-defined pulse template into a test substance, receiving a resultant ultrasound reflection signal from the test substance, comparing the received signal against a reference signal to generate a response signal, comparing the response signal against a selection criterion and selecting, as a pre-defined pulse template that the sensing apparatus is to be capable of using, the pre-defined pulse template that performs best against the selection criterion; and materially producing the apparatus so designed.

The test substance may be air. The test substance may be a solid.

The method may comprise selecting two or more pre-defined pulse templates for the sensing apparatus by driving each of the pre-defined pulse templates into two or more different test substances and selecting, for each test substance, a pre-defined pulse template that performed best against the selection criterion.

The method may comprise selecting two or more pre-defined pulse templates for the sensing apparatus by comparing the response signal for each pre-defined pulse template against two or more different selection criterion and selecting, for each selection criterion, a pre-defined pulse template that performed best against that criterion.

The method may comprise materially producing the apparatus by storing the selected pulse template in a memory of the sensing apparatus.

DESCRIPTION OF THE DRAWINGS

The present invention will now be described by way of example with reference to the accompanying drawings. In the drawings.

DETAILED DESCRIPTION

Figure 1:
FIGS. 1a to h show examples of different pulse templates.
Figure 1:
Figure 1:
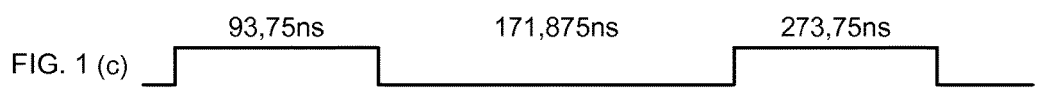
Figure 1:
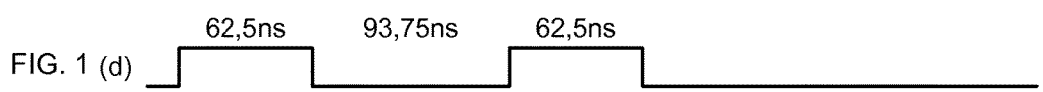
Figure 1:
Figure 1:
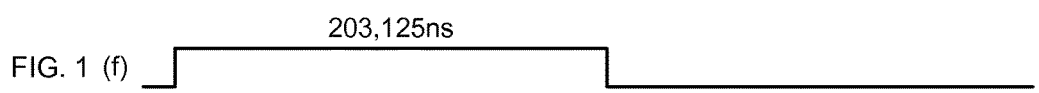
Figure 1:
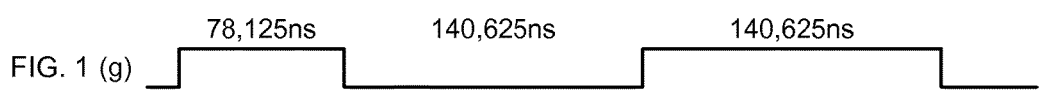
Figure 1:
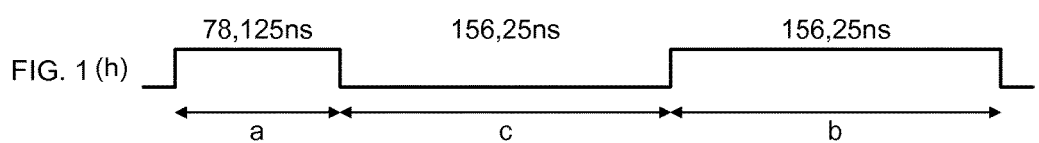

A sensing apparatus has an ultrasound transceiver for transmitting ultrasound signals into a sample and receiving reflections of those signals from the sample. The sensing apparatus also includes a detector for detecting the reflections. The detection process is made more straightforward if the ultrasound signals have some predefined shape so that the detector knows approximately what the reflections should look like. The sensing apparatus has a driver, which is capable of generating a predefined pulse template for use by the transceiver in generating the ultrasound signal, so that the resulting ultrasound signal consists of pulses whose shape is at least approximately known to the sensing apparatus.

The detector detects reflections by comparing the received signal against a reference signal. This process generates a response signal, which comprises values as a function of time that represents the strength of the match between the received signal and the reference signal at the respective time. The detector can use the response signal to determine when a reflection was received at the transceiver and also some measure of the signal energy comprised in that reflection. Both of these measures are useful to the apparatus as they indicate the time-of-flight of the reflection (so how deep in the sample the structural feature that triggered the reflection is located) and can also give an indication of the type of material through which the reflection has traveled.

The information that is gathered by the sensing apparatus is likely to be more accurate the more accurately the reflections are detected by the detector. The exact shape of the transmitted ultrasound signals is, in practice, known only approximately to the detector because the pulse templates inevitably undergo some unquantifiable changes on being converted into an analogue signal and then output as an ultrasound signal. The inventors have found through practical experimentation that some pulse shapes are detected more accurately than others, and also that a particular pulse shape's performance can vary depending of the type of material in the sample and the structural feature that is being scanned. Experiments have also indicated that although some pulse shapes produce different outputs at the scanning apparatus, other pulse shapes produce outputs that are virtually indistinguishable from each other. Examples of different pulse templates are shown in FIGS. 1(a) to (h) and include templates that consist of only one pulse, or more than one pulse, of various durations. It is also possible for a pulse template to consist of a single "step" from low-to-high or from high-to-low. A pulse may include both an increasing and a decreasing step.

A sensing apparatus is preferably provided with two or more different pulse templates so that an appropriate pulse template can be selected for the particular sample. The pulse templates preferably perform: (a) differently from each other; and (b) optimally for an intended application of the scanning apparatus, which implies that a specific selection criteria are needed. The inventors have found that the performance of a particular pulse template can be predicted by computing a number of different metrics based on a response signal the pulse template generates when driven into air or a test sample. The driver of the sensing apparatus is therefore preferably configured to generate a plurality of pre-defined pulse templates that include at least two of the following:

i) a pulse template that consists of a single pulse and that, when the transceiver is being driven into air, generates a response signal having a higher prominence of a primary peak than the response signals generated by any of the other pre-defined pulse templates that consist of a single pulse;

ii) a pulse template that consists of two or more pulses and that, when the transceiver is being driven into air, generates a response signal having a higher prominence of a primary peak than the response signals generated by any of the other pre-defined pulse templates;

iii) a pulse template that, when the transceiver is being driven into a solid, generates a response signal having a higher prominence of a primary peak than the response signals generated by any of the other pre-defined pulse templates; and iv) a pulse template that generates a response signal having a higher proportion of its energy in a primary peak than the response signals generated by any of the other pre-defined pulse templates.

To illustrate the differences between the different pulse templates: pulse template (i) works particularly well for thin carbon plates; pulse template (ii) works particularly well for imaging boreholes (but also performs well on impact damage and other applications); pulse template (iii) works particularly well for imaging impact damage (but also performs well on boreholes and other applications); and pulse template (iv) works particularly well for metal or metal-like samples.

The apparatus will now be described in more detail with reference to a particular example. This is for illustrative purposes only, and it should be understood that the apparatus is not limited to any specific feature of this example.

Figure 2:
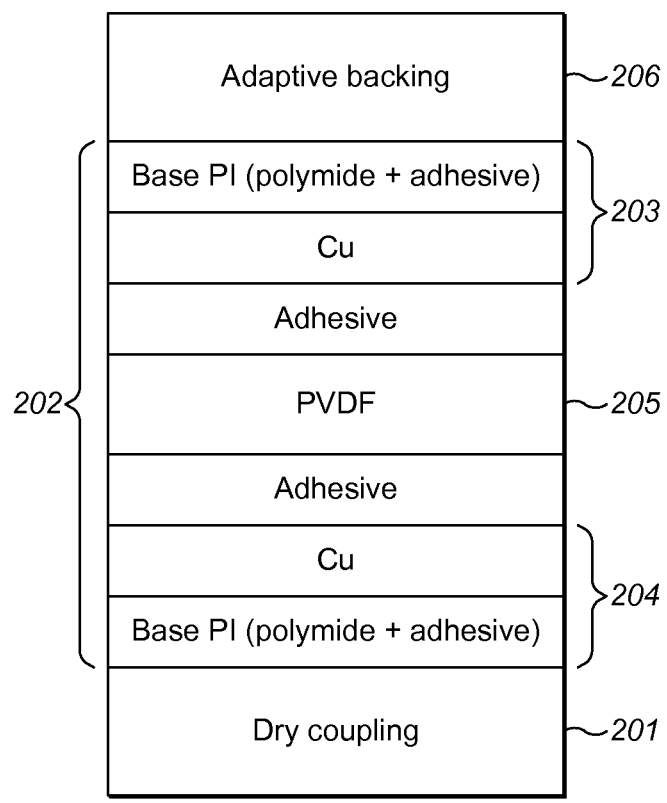
FIG. 2 shows an example of an ultrasound transceiver.

An example of an ultrasound transceiver is shown in FIG. 2. The dry coupling 201 may be formed of an elastomer or any other suitable material. The outer surface of the dry coupling is applied to a sample when testing is to be done. Behind the dry coupling is a transducer laminate 202. It is comprised of transmitter 203 and receiver 204 circuits that are respectively formed of copper deposited on a polyimide film. Each copper layer may form a series of electrodes. The electrodes might also be formed of other materials—gold, for example. A layer of piezoelectric material 205 (PVDF in this example) is sandwiched between the copper layers. This layer generates ultrasound signals when a high-voltage pulse train is sent out on the transmitter electrode, causing the piezoelectric layer to start vibrating and output an ultrasonic wave. In other examples the transducer might not comprise the adhesive or base film layers. The electrodes might be deposited directly on the piezoelectric layer.

The high-voltage pulse train is generated using a pulse template. Typically the pulse template is a digital signal that is then converted into the analogue, high voltage pulse train by the driver. This conversion may introduce small changes into the shape of the pulses. Also, the rise and fall times and transmit delay of the transmitter are usually specific to the transceiver and are largely unknown because of the unknown responsiveness of the piezoelectric layer to the high-voltage pulse train. These are two of the reasons why it is difficult to optimise the performance of the apparatus using the shape of the pulse template alone, because that pulse template will inevitably not be exactly what is transmitted as an ultrasound pulse. Therefore, it is preferable to select particular pulse templates based on their actual performance in accordance with quantifiable metrics.

In one example the transmitter and receiver circuits comprise a plurality of elongated electrodes deposited in parallel lines on a flexible base layer. The transmitter and receiver circuits may be laminated together. They may be arranged so that their respective electrodes overlap at right angles to form an intersecting pattern. The intersections form an array of transducer elements.

The number of transmitter and receiver electrodes is scalable. Hence transducers can be designed of any desired size and shape. The electrode width is also scalable to adjust the amount of energy output per electrode. The electrode width can also be adjusted in dependence on the desired focus. The distance between the electrodes might also be varied. Generally it is preferred to have small gaps between neighbouring electrodes to maximise ultrasound energy by stimulating as large an area of the piezoelectric layer as possible. The thickness of the electrodes may be chosen to control factors such as frequency, energy and beam focus. The thickness of the base film may be chosen to control factors such as signal shape, frequency and energy. The PVDF thickness can also be adapted to change signal shape, frequency and energy (which are also dependent on the transmitting pulse shape). The dry coupling thickness can be adapted to create a particular time lag between transmitting the ultrasound pulses and receiving reflections of them from the sample.

Figure 3:
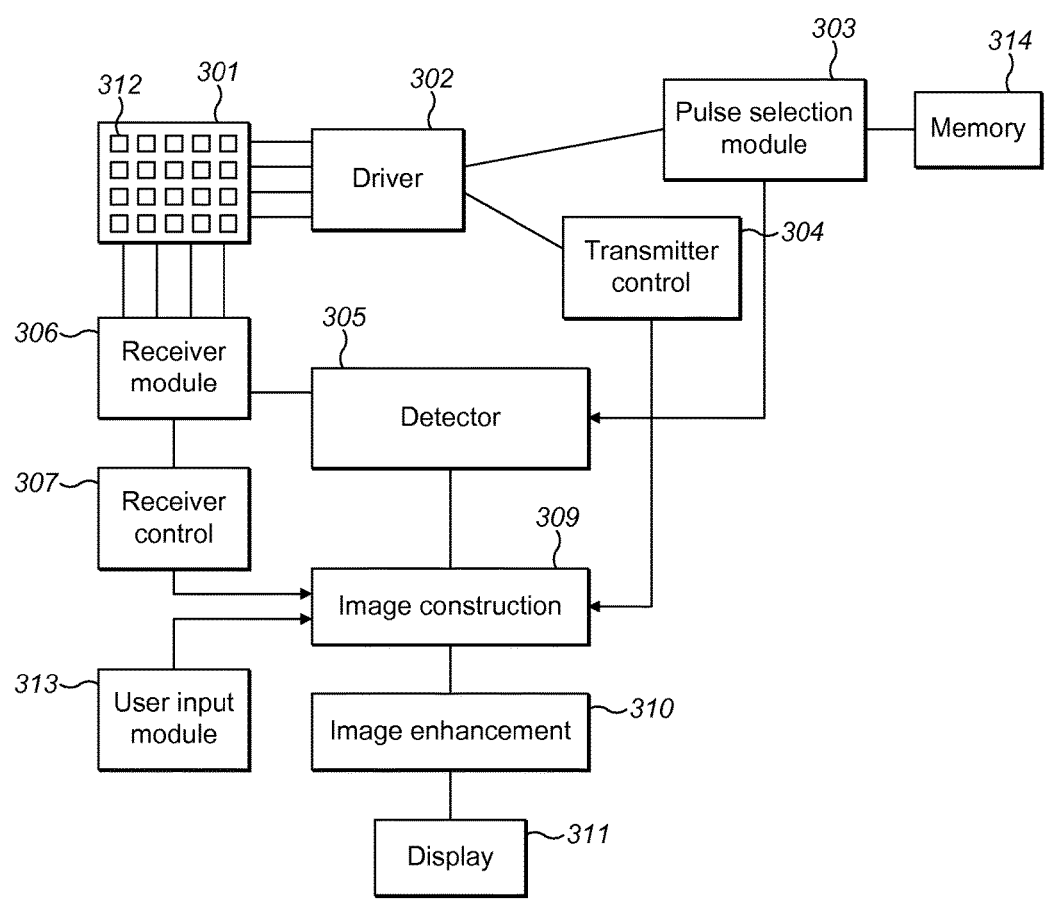
FIG. 3 shows an example of a sensing apparatus.

An example of a sensing apparatus is shown in FIG. 3. In this example the transmitter and receiver are implemented by an ultrasound transducer 301, which comprises a matrix array of transducer elements 312. These transducer elements form the receiver surface. The transmitter electrodes are connected to the driver 302, which supplies a pulse template to a particular electrode. The transmitter control 304 selects the transmitter electrodes to be activated. The receiver electrodes sense sound waves that are emitted from the object. The receiver module 306 receives and amplifies these signals.

The transmitter may transmit the sound pulses using signals having frequencies between 100 kHz and 30 MHz, preferably between 1 and 15 MHz and most preferably between 2 and 10 MHz.

The pulse selection module 303 and pulse generator 313 operate under the control of the driver. The pulse selection module selects the particular pulse shape to be transmitted. Usually this selection will be based on user input but it could be made automatically by the apparatus in dependence on a particular application (e.g. a particular structural feature to be scanned) or a material of the sample. The pulse generator supplies the transmitter module with an analogue pulse pattern that will be converted into ultrasonic pulses by the transducer. The pulse selection module may have access to a plurality of predefined pulse templates stored in memory 314.

Figure 7:
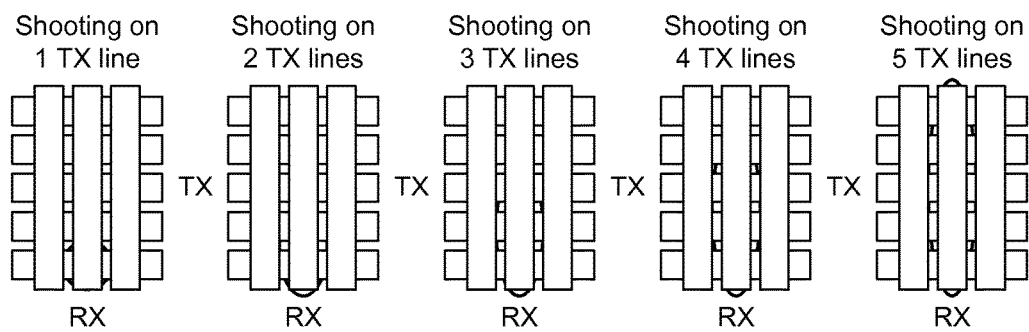
FIG. 7 shows an example of how to activate multiple transmit lines in an ultrasound transducer.
Figure 7:
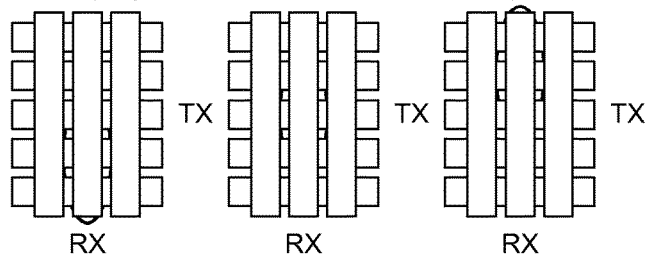
Figure 7:
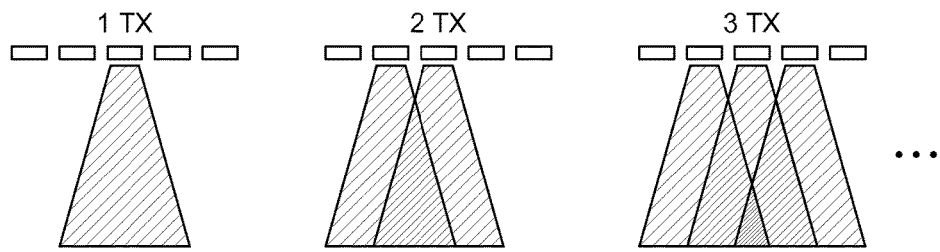

The apparatus alternately transmits and receives. When setting up a receive line and transmitting a pulse on a transmit line, an acoustic wave is generated in the area of overlap (the transducer element). This sound wave travels through a coupling pad and into the material for inspection. The reflection of the sound wave is picked up by the same receive line that was set up during transmission. The transmit lines may be activated individually in turn. Another option is for the transmit lines to be activated in groups, which provides more ultrasound energy and can provide better focus at certain depths. An example of this is shown in FIG. 7: each transmit operation activates a plurality of transmit lines and each transmit operation in the sequence overlaps the previous sequence by at least one transmit line. The transmit operations progress line-by-line so that each transmit operation is one transmit operation further across the matrix than the preceding operation. Each element in the ultrasound transducer may obtain 2 to 4 time series by repeated measurement. Each of these time series may be processed in accordance with the signal processing methods described below.

The detector 305 processes the received ultrasound signals detect reflected sound pulses and extract relevant information from the reflections. The detector may be implemented by a signal processor. The signal is suitably time-gated so that the signal processor only detects and processes reflections from depths of interest. The time-gating may be adjustable, preferably by a user, so that the operator can focus on a depth range of interest. The depth range is preferably 0 to 20 mm, and most preferably 0 to 15 mm. The signal processor may receive a different signal from each location on the receiver surface, e.g. at each transducer element. The signal processor may analyse these signals sequentially or in parallel.

The signal processor suitably detects reflected pulses by comparing the received signal with a reference signal. The reference signal may be representative of the selected pulse template. There are a number of ways this may be achieved. A preferred method is to use a match filter corresponding to the selected pulse template (more information about how the match filter may be generated is given below). The apparatus may be arranged to accumulate and average a number of successive samples in the incoming sample for noise reduction before the filtering is performed. The analysis unit uses the match filter to accurately determine when the reflected sound pulse was received. The signal processor performs features extraction to capture the maximum amplitude of the filtered signal and the time at which that maximum amplitude occurs. The signal processor may also extract phase and energy information.

The signal processor is preferably capable of recognising multiple peaks in each received signal. It may determine that a reflection has been received every time that the output of the match filter exceeds a predetermined threshold. It may identify a maximum amplitude for each acknowledged reflection.

Figure 4A:
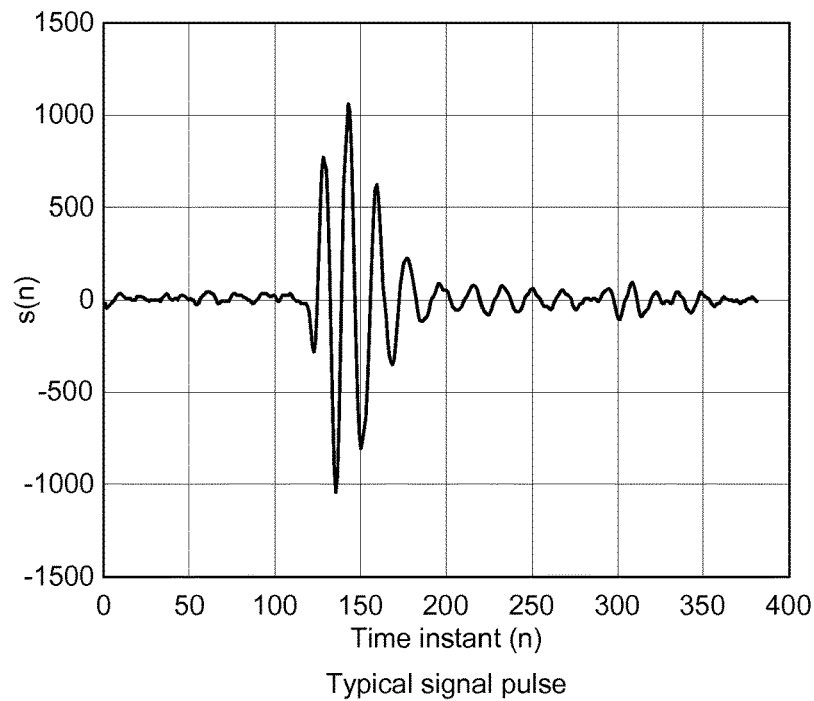
FIGS. 4a to c show an example of an ultrasound signal, a match filter and a response signal.
Figure 4B:
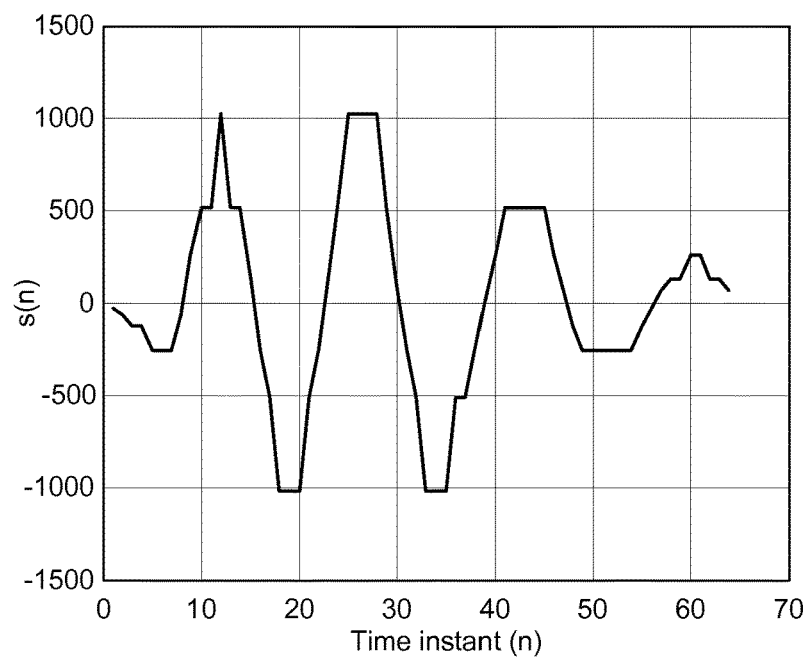
Figure 4C:
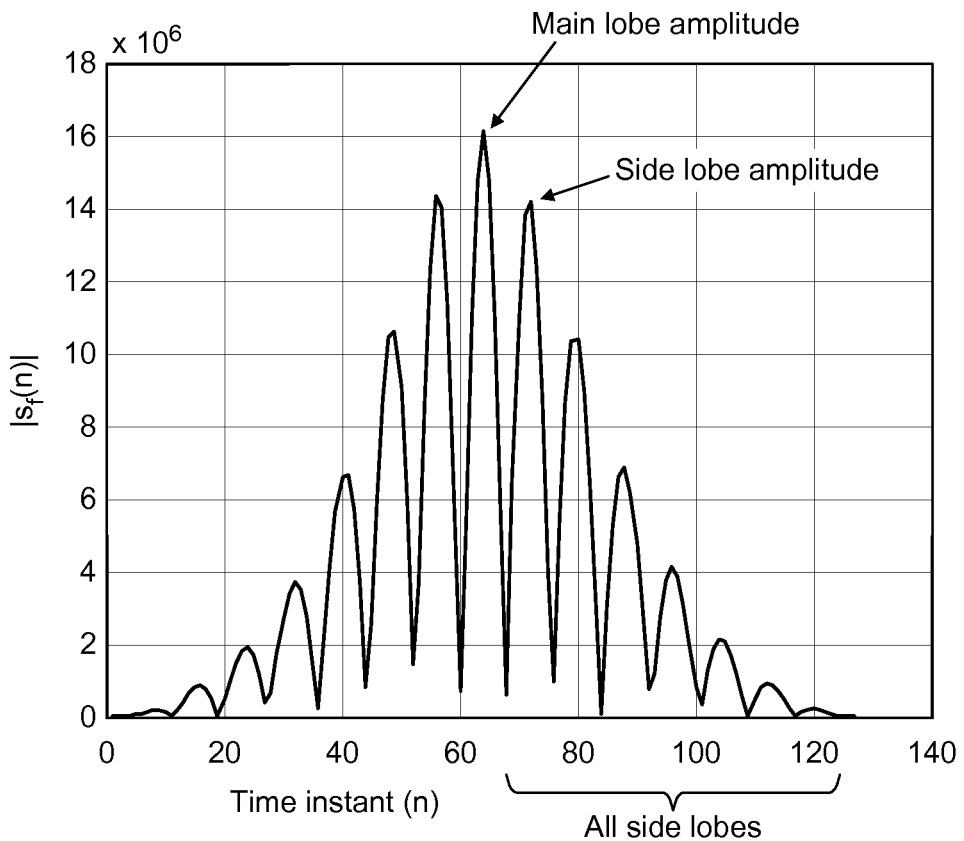

Examples of an ultrasound signal s(n) and a corresponding match filter p(n) are shown in FIGS. 4a and b respectively. The ultrasound signal s(n) is a reflection of a transmitted pulse against air. The absolute values of the filtered time series (i.e. the absolute of the output of the match-filter) for ultrasound signal s(n) and corresponding match filter p(n) are shown in FIG. 4c. This is the response signal. The signal processor estimates the time-of-flight as the time instant where the amplitude of the filtered time series is at a maximum. In this example, the time-of-flight estimate is at time instant 64.

In one embodiment the apparatus may amplify the filtered signal before extracting the maximum amplitude and time-of-flight values. This amplification may be done by the signal processor. The amplification might also be controlled by a different processor or FPGA. In one example the time corrected gain is an analogue amplification. This may compensate for any reduction in amplitude that is caused by the reflected pulse's journey back to the receiver. One way of doing this is to apply a time-corrected gain to the filtered signal. The amplitude with which a sound pulse is reflected by a material is dependent on the qualities of that material (for example, its acoustic impedance). Time-corrected gain can (at least partly) restore the signal to what it would have looked like when first reflected. The resulting image should then more accurately reflect the material properties of the structural feature that reflected the pulse. The resulting image should also more accurately reflect any differences between the material properties of the structural features in the object.

The image construction module may be configured to receive user input from user input module 313. Generated images are output to display 311, which may be contained in the same device or housing as the other components or in a separate device or housing. The display may be linked to the other components via a wired or wireless link.

Some or all of the image construction module and the image enhancement module could be comprised within a different device or housing from the transmitter and receiver components, e.g. in a tablet, PC, PDA or other computing device. However, it is preferred for us much as possible of the image processing to be performed in the transmitter/receiver housing (see e.g. handheld device 601 in FIG. 6).

The image construction module may generate a number of different images using the information gathered by the signal processor. Any of the features extracted by the signal processor from the received signal may be used. Typically the images represent time-of-flight, energy, amplitude and/or phase. The image construction module may associate each pixel in an image with a particular location on the receiver surface so that each pixel represents a reflection that was received at the pixel's associated location.

The image construction module may be able to generate an image from the information gathered using a single transmitted pulse. The image construction module may update that image with information gathered from successive pulses. The image construction module may generate a frame by averaging the information for that frame with one or more previous frames so as to reduce spurious noise. This may be done by calculating the mean of the relevant values that form the image.

The selection of the pulse templates for the sensing apparatus could be performed by the apparatus itself. The apparatus may have many pulse templates available to it, which it can test in turn. This kind of calibration process might require the involvement of a user, e.g. by firing the sensing apparatus against air and then against a solid sample of appropriate material. It is more convenient, however, for the pulse template selection to form part of a design and manufacture process that produces a sensing apparatus as its end result. An example of such a process is shown in FIG. 5.

Figure 5:
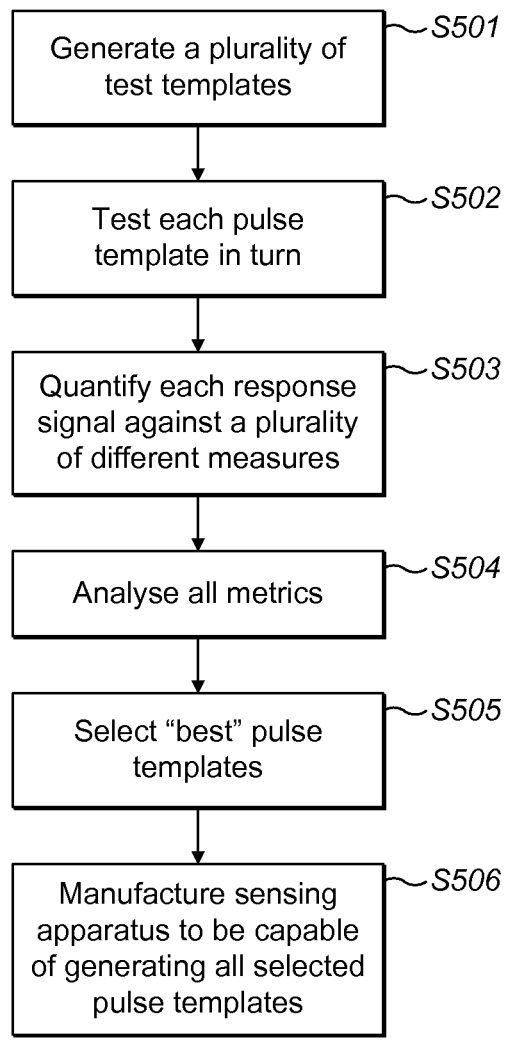
FIG. 5 shows an example of a design and manufacture process.

In step S501 of FIG. 5 a plurality of pulse templates are generated for testing. Each pulse template may contain one or more individual pulses, which may have different shapes, amplitudes and durations. Various examples are shown in FIG. 1. As an example, the pulse template shown in FIG. 1(h) consists of two separate digital pulses. The distances a, b and c represent the respective durations of the first pulse, the second pulse and the time between the two pulses. A large number of different pulse templates may be generated by having "a", "b" and "c" vary. For example, with a 64 MHz clock, "a" and "b" might each vary between 4 and 15 clock cycles and "c" might vary between 6 and 15 clock cycles. In step S502 each of the pulse templates is tested in turn. Each pulse template may go through multiple different rounds of testing, as described in more detail below. The tests may involve driving the pulse templates into different substances, such as air or a solid of an appropriate material. The response signal from each test is quantified according to a number of different metrics (step S503). The results across all pulse templates and all rounds of testing are then analysed (step S504) and the optimum pulse templates are selected for the sensing apparatus (step S505). The optimum pulse templates will usually depend on what applications the apparatus is intended for. In step S506 the sensing apparatus is manufactured to have the capability to generate the selected pulse templates.

The design process may involve using a sensing apparatus such as that described above to assess the relative performance of the different pulse templates against the different selection criteria. This helps to give an accurate impression of how the pulse templates will perform in practice when generated by one of the sensing apparatus. The design process is, however, likely to incorporate additional processing power in the form of computers etc so that a large number of different pulse templates can be assessed reasonably quickly.

One additional step that may be incorporated into the selection method is a step of generating match filters corresponding to the different pulse templates. The match filter should ideally be similar in shape to a reflection of the transmitted pulse template. The exact shape of the reflection is typically not known in advance (e.g. because the transmitted pulse will not be exactly the same shape as the pulse template, as explained above). One possibility is to carry out simulations to predict the shape of the reflections. Another option is to look at the shape of the reflections in practice. For example, the pulse template may be driven into a sample. That sample suitably has a known depth so that the time at which the reflection can be expected is known. A section of the received signal may then be selected as representing the reflection of the pulse template. A suitable section might be, for example, 64 samples long. This section then forms the basis of the match filter for that pulse template. In one example, the coefficients for the match filter may be quantised to the nearest power-of-two so that the multiplication operations can be reduced to simple binary left-shift operations.

In one example there may be three rounds of testing. In round one, ultrasound generated using pulse templates having any number of pulses is fired towards air and the "best" pulse template is selected in accordance with any desired criterion. In round two, the ultrasound signals are again fired towards air, but in this instance the pulse templates are restricted to those consisting of just one pulse. In round three, ultrasound generated using pulse templates having any number of pulses is fired into a sample. The sample is suitably of the same or a similar material to that with which the eventual apparatus is expected to be used. Typically the reflection that is tested against the selection criteria is the reflection from the back wall of the solid sample. The time at which that reflection is expected is usually known in advance since the thickness of the sample will be known, as will the speed of sound in that material.

The criteria against which the pulse templates are evaluated may include one or more of the following, as applied to the received reflection:

- The ratio between the main lobe amplitude and the maximum absolute side lobe amplitude.
- The difference between the main lobe amplitude and the maximum absolute side lobe amplitude.
- The difference between the main lobe amplitude and the maximum absolute side lobe amplitude, normalized with root-mean-square (RMS) of the matched filter coefficients.
- The main lobe amplitude divided by the mean absolute energy of all side lobes.
- The main lobe amplitude divided by the average absolute amplitude of all side lobes.
- The main lobe amplitude minus the average absolute amplitude of all side lobes, normalized with the RMS of the matched filter coefficients.
- The signal-to-noise ratio (SNR), i.e. the amplitude of the main lobe divided by the RMS of the filter coefficients.
- The bandwidth of the signal. This may be calculated using the derivative of a smoothing spline approximation of the ultrasound signal.
- The variance of the estimated time-of-flight.
- The lowest amplitude of any occupied frequency bin in an FFT performed on the response signal. This criteria may be modified by setting a minimum threshold so that the selected pulse template is the one with an occupied frequency bin having the lowest amplitude above the minimum threshold rather than the lowest amplitude per se. The selected pulse template is therefore the one having the lowest amplitude peak above a certain value, where the certain value is zero or above.
- A scheme that applies image-based criteria, i.e. criteria related to the quality of the processed ultrasound image, such as noise, degree of blurring, etc.

Variations of the above criteria may only consider positive side-lobes. (e.g. "the ratio between the main lobe amplitude and the maximum positive side lobe amplitude") might also be used. Another options is to combine two or more pulse templates and filters. For instance, one pulse template may be transmitted and filtered with a corresponding filter, then a second, different pulse template may be transmitted and filtered with the corresponding match filter. The two filtered time series are then averaged, and the criteria are computed on the averaged time series. This scheme searches for the best pulse pair for each criterion.

In general, pulse templates that perform well against criteria that measure the prominence of the primary peak tend to perform well in practice. The first seven criteria listed above fall into this category. Pulse templates that show a high proportion of their energy in the primary peak (a criterion which is also a member of the "prominence" category) tend to perform particularly well in practice. Outside of the "prominence" category, good results have been found with pulse templates that perform well in accordance with the "FFT" criterion.

Preferably a sensing apparatus is capable of using two or more different pulse templates. In order that the sensing apparatus is adaptable to different applications, those pulse templates are preferably selected according to different criteria. The sensing apparatus described above is capable of generating at least two pulse templates, but it could equally be capable of generating three, four or more pulse templates.

As an example, the following eight pulse templates were selected during the three rounds of testing described above:

Pulse template 1: the pulse template that generated the highest main lobe to side lobe ratio in round 1.
Pulse template 2: the pulse template that generated the highest difference between the main lobe amplitude and side lobe amplitude in round 1.
Pulse template 3: the pulse template that generated the highest SNR in round 1.
Pulse template 4: the pulse template that generated the highest ratio of the main lobe amplitude to the mean absolute energy of all side lobes in round 1.
Pulse template 5: the pulse template that generated the highest main lobe to side lobe ration in round 2.
Pulse template 6: the pulse template that generated the highest difference between the main lobe amplitude and side lobe amplitude in round 2.
Pulse template 7: the pulse template that generated the highest difference between the main lobe amplitude and side lobe amplitude in round 3 (in this example the solid was a CFRP (carbon-fiber-reinforced polymer)).
Pulse template 8: the pulse template that generated the FFT with the lowest amplitude occupied frequency bin.

The performance of a particular pulse template may be assessed in practice in dependence on the quality of the images it generates. To a certain extent this is subjective, but there are various qualitative assessments that can be made of image quality, such as whether a structural feature having particular dimensions or located at a particular depth is visible in the image, and how accurately the location and size of a structural feature within a sample can be determined from the image. It has been found that some pulse templates produce outputs that are virtually indistinguishable from each other (for example, pulse templates that perform "best" according to different ones of the "prominence" criteria in a particular test round generally perform similarly in practice). Preferably a sensing apparatus is capable of generating pulse templates that actually perform differently in practice (in addition to having been selected in accordance with different criteria).

To return to the example above, the eight selected pulse templates tended to group together in terms of their practical performance: (i) pulse templates 1 and 2 perform similarly and work particularly well for imaging impact damage, but also for boreholes and other applications; (ii) pulse templates 3, 7 and 8 perform similarly and work particularly well for imaging boreholes, but also for impact damage and other applications; (iii) pulse templates 5 and 6 perform similarly and work particularly well for thin carbon plates; (iv) pulse template 4 is the most different from the other templates and works best on metals or metal-like materials. An apparatus capable of generating two or more of: (i) either pulse template 1 or 2; (ii) any of pulse templates 3, 7 or 8; (iii) either pulse template 5 or 6; and (iv) pulse template 4 has been found to have a good range of pulse templates for automotive/aerospace applications. An apparatus may produce any three of, or all four of those last groups (i) to (iv).

Figure 6:
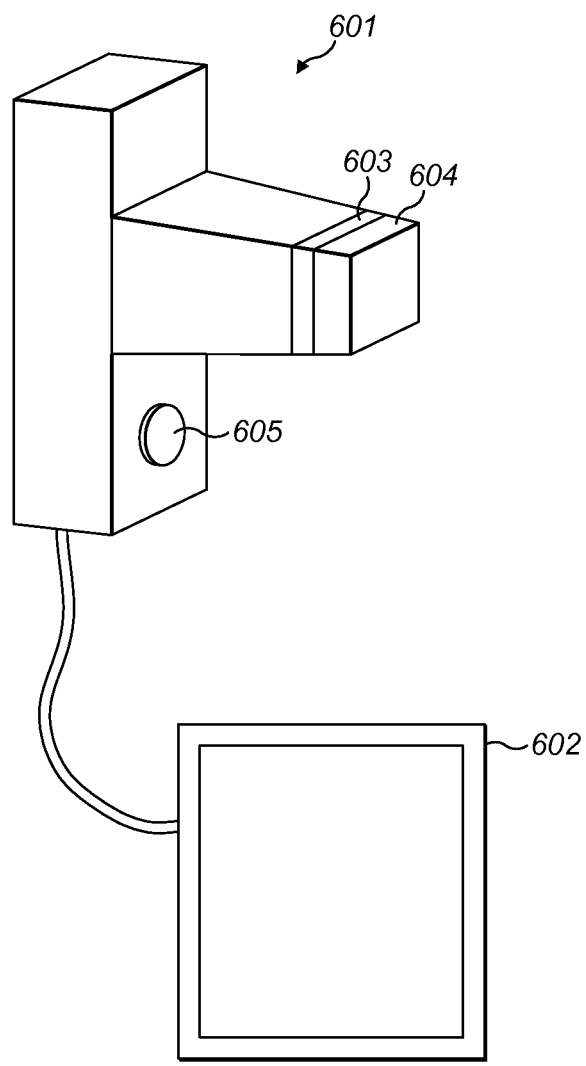
FIG. 6 shows an example of a handheld sensing apparatus.

An example of a handheld device for imaging below the surface of an object is shown in FIG. 6. The device 601 could have an integrated display, but in this example it outputs images to a tablet 602. The device could also output to any suitable display, including a PC, laptop, pda, wearable displays etc. The connection with a separate could be wired, as shown, or wireless. The device has a matrix array 603 for transmitting and receiving ultrasound signals. Suitably the array is implemented by an ultrasound transducer comprising a plurality of electrodes arranged in an intersecting pattern to form an array of transducer elements. The transducer elements may be switched between transmitting and receiving. The handheld apparatus comprises a dry coupling layer 604 for coupling ultrasound signals into the object. The dry coupling layer also delays the ultrasound signals to allow time for the transducers to switch from transmitting to receiving. A dry coupling layer offers a number of advantages over other imaging systems, which tend to use liquids for coupling the ultrasound signals. This can be impractical in an industrial environment. If the liquid coupler is contained in a bladder, as is sometimes used, this makes it difficult to obtain accurate depth measurements, which is not ideal for non-destructive testing applications.

The matrix array 603 is two dimensional so there is no need to move it across the object to obtain an image. A typical matrix array might be 30 mm by 30 mm but the size and shape of the matrix array can be varied to suit the application. The device may be straightforwardly held against the object by the operator. Commonly the operator will already have a good idea of where the object might have sub-surface flaws or material defects; for example, a component may have suffered an impact or may comprise one or more drill or rivet holes that could cause stress concentrations. The device suitably processes the reflected pulses in real time so the operator can simply place the device on any area of interest.

The handheld device also comprises a dial 605 that the operator can use to change the pulse shape and corresponding match filter. The most appropriate pulse shape may depend on the type of structural feature being imaged and where it is located in the object. The operator views the object at different depths by adjusting the time-gating via the display. Having the apparatus output to a handheld display, such as tablet 602, or to an integrated display, is advantageous because the operator can readily move the transducer over the object, or change the settings of the apparatus, depending on what he is seeing on the display and get instantaneous results. In other arrangements, the operator might have to walk between a non-handheld display (such as a PC) and the object to keep rescanning it every time a new setting or location on the object is to be tested.

The apparatus and methods described herein are particularly suitable for analysing bonding, for detecting debonding and delamination in composite materials such as carbon-fibre-reinforced polymer (CFRP). This is important for aircraft maintenance. It can also be used detect flaking around rivet holes, which can act as a stress concentrator. The apparatus is particularly suitable for applications where it is desired to image a small area of a much larger component. The apparatus is lightweight, portable and easy to use. It can readily carried by hand by an operator to be placed where required on the object.

Another application is in performing medical examinations. It is known to examine patients using ultrasound in order to image features within the patient's body. Typically, this requires a degree of specialisation on the part of the operator in order to tune the operating parameters of the ultrasound equipment to develop a reliable image. For example, the operator may need to adjust the equipment to account for features of the patient such as the properties of their skin, particularly the depth of the patient's subcutaneous fat in the region of the examination. By providing an ultrasound inspection device having a series of pre-defined pulse programs, of the type described above, it can be possible for a non-specialised person to perform a more reliable ultrasound inspection. The user can select from the pre-defined programs one that produces acceptable results for the patient in question. The set of pulse programs described herein may be particularly useful for imaging features associated with the patient's skin, for example skin cancers, lipomas and subcutaneous lesions. Such a system can allow ultrasound inspections to be performed by nursing staff or general practitioners rather than specialists in medical imaging, reducing cost and the need for biopsies.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A sensing apparatus comprising:
   an ultrasound transceiver for transmitting ultrasound signals into a sample and receiving a resultant ultrasound reflection signal from the sample;
   a detector for processing signals received by the transceiver by comparing the received signal against a reference signal to generate a response signal, the response signal comprising values as a function of time that represent the strength of the match between the received signal and the reference signal at the respective time; and
   a driver capable of generating a plurality of pre-defined pulse templates, the driver being operable in a use phase to apply a selected one of the pre-defined pulse templates to the transceiver for driving it to transmit ultrasound signals, the pre-defined pulse templates being such as to include at least two of the following:
   i) a pulse template having been selected in a pre-use phase that consists of a single pulse and that, when the transceiver is driven directly into air in the pre-use phase, generates a response signal having a higher prominence of a primary peak than the response signals generated by any of the other pre-defined pulse templates that consist of a single pulse;
   ii) a pulse template having been selected in the pre-use phase that consists of two or more pulses and that, when the transceiver is driven directly into air in the pre-use phase, generates a response signal having a higher prominence of a primary peak than the response signals generated by any of the other pre-defined pulse templates;

iii) a pulse template having been selected in the pre-use phase that, when the transceiver is being driven into a solid in the pre-use phase, generates a response signal having a higher prominence of a primary peak than the response signals generated by any of the other pre-defined pulse templates; and iv) a pulse template having been selected in the pre-use phase that, when the transceiver is driven in the pre-use phase, generates a response signal having a higher proportion of its energy in a primary peak than the response signals generated by any of the other pre-defined pulse templates.

2. A sensing apparatus as claimed in claim 1, in which pulse template (i) generates a response signal in which the ratio of the amplitude of its primary peak to the amplitude of its largest side lobe is higher than in the response signals generated by any of the other pre-defined pulse templates that consist of a single pulse.

3. A sensing apparatus as claimed in claim 1, in which pulse template (i) generates a response signal in which the difference between the amplitude of its primary peak and the amplitude of its largest side lobe is larger than in the response signals generated by any of the other pre-defined pulse templates that consist of a single pulse.

4. A sensing apparatus as claimed in claim 1, in which pulse template (ii) generates a response signal in which the ratio of the amplitude of its primary peak to the amplitude of its largest side lobe is higher than in the response signals generated by any of the other pre-defined pulse templates.

5. A sensing apparatus as claimed in claim 1, in which pulse template (ii) generates a response signal in which the difference between the amplitude of its primary peak and the amplitude of its largest side lobe is larger than in the response signals generated by any of the other pre-defined pulse templates.

6. A sensing apparatus as claimed in claim 1, in which pulse template (iii) generates a response signal in which the ratio of the amplitude of its primary peak to the amplitude of its largest side lobe is higher than in the response signals generated by any of the other pre-defined pulse templates.

7. A sensing apparatus as claimed in claim 1, in which pulse template (iv) generates a response signal in which the ratio of the amplitude of its primary peak to the mean absolute energy comprised in its side lobes is higher in than the response signals generated by any of the other pre-defined pulse templates.

8. A sensing apparatus as claimed in claim 1, in which the pre-defined pulse templates include: (v) a pulse template that generates a response signal having an FFT that has an occupied frequency bin with an amplitude that is above a certain value but which is lower than the amplitude of any occupied frequency bin above the certain value in the FFTs of the response signals generated by any of the other pre-defined pulse templates.

9. A sensing apparatus as claimed in claim 1, comprising a user input device configured to receive a user input for selecting one of the pre-defined pulse templates to be applied to the transceiver.

10. A sensing apparatus as claimed in claim 1, the detector being configured to compare the received signal against a reference signal that is selected in dependence on the selected pulse template.

11. A sensing apparatus as claimed in claim 10, the detector being configured to compare the received signal against a match filter.

12. A sensing apparatus as claimed in claim 1, in which the pre-defined pulse templates include a pulse template consisting of two or more pulses of the same length.

13. A sensing apparatus as claimed in claim 1, in which the pre-defined pulse templates include a pulse template consisting of two or more pulses in which the length of one of those pulses is different from the length of at least another of those pulses.

14. A sensing apparatus as claimed in claim 1, in which the pre-defined pulse templates include a pulse template consisting of a single step.

15. A method of manufacturing a sensing apparatus comprising:
designing the apparatus, including:
testing a plurality of pre-defined pulse templates by driving each pre-defined pulse template into a test substance in a pre-use phase;
receiving a resultant ultrasound reflection signal from the test substance;
comparing the received signal against a reference signal to generate a response signal;
comparing the response signal against a selection criterion; and
selecting, as a pre-defined pulse template that the sensing apparatus is to be capable of using, the pre-defined pulse template that performs best against the selection criterion for use in a use phase;
and materially producing the apparatus so designed.

16. A method as claimed in claim 15, in which the test substance is air.

17. A method as claimed in claim 15, in which the test substance is a solid.

18. A method as claimed in claim 15, the method comprising selecting two or more pre-defined pulse templates for the sensing apparatus by driving each of the pre-defined pulse templates into two or more different test substances and selecting, for each test substance, a pre-defined pulse template that performed best against the selection criterion.

19. A method as claimed in claim 15, the method comprising selecting two or more pre-defined pulse templates for the sensing apparatus by comparing the response signal for each pre-defined pulse template against two or more different selection criterion and selecting, for each selection criterion, a pre-defined pulse template that performed best against that criterion.

20. A method as claimed in claim 15, the method comprising materially producing the apparatus by storing the selected pulse template in a memory of the sensing apparatus.

21. A sensing apparatus as claimed in claim 1, in which the ultrasound transceiver comprises a plurality of transmit lines for transmitting ultrasound signals into the sample, the sensing apparatus being configured to activate the transmit lines in groups.

22. A sensing apparatus as claimed in claim 21, in which the sensing apparatus is configured to perform a sequence of transmit operations, each transmit operation in the sequence of transmit operations causing the activation of a respective group of transmit lines which overlaps the group of transmit lines activated in the preceding transmit operation by at least one transmit line.

* * * * *